(12) United States Patent
Körner et al.

(10) Patent No.: US 9,211,135 B2
(45) Date of Patent: Dec. 15, 2015

(54) ENDOSCOPIC INSTRUMENT

(75) Inventors: Eberhard Körner, Knittlingen (DE);
Franc Schmid, Neulingen (DE);
Stephan Prestel, Rheinstetten-Mörsch (DE)

(73) Assignee: Richard Wolf GmbH, Knittlingen (DE)

( * ) Notice: Subject to any disclaimer, the term of this patent is extended or adjusted under 35 U.S.C. 154(b) by 623 days.

(21) Appl. No.: 12/175,713

(22) Filed: Jul. 18, 2008

(65) Prior Publication Data
US 2009/0023988 A1 Jan. 22, 2009

(30) Foreign Application Priority Data
Jul. 20, 2007 (EP) .................. 07 014 255

(51) Int. Cl.
*A61B 17/16* (2006.01)
*A61B 17/32* (2006.01)
*A61B 17/29* (2006.01)

(52) U.S. Cl.
CPC ....... *A61B 17/32002* (2013.01); *A61B 17/1624* (2013.01); *A61B 17/1633* (2013.01); *A61B 2017/2927* (2013.01); *A61B 2017/320032* (2013.01)

(58) Field of Classification Search
CPC ............... A61B 17/320016; A61B 17/32002; A61B 2017/32002; A61B 2017/32004; A61B 2017/00318; A61B 17/1624; A61B 17/1633; A61B 17/1615; A61B 17/320758; A61B 1/0051; A61B 1/0056; A61B 1/0057; A61B 1/008

USPC ............. 606/79, 80, 167, 170, 180; 600/564, 600/568
See application file for complete search history.

(56) References Cited

U.S. PATENT DOCUMENTS

| | | | | |
|---|---|---|---|---|
| 815,726 | A * | 3/1906 | Mehlig | 464/147 |
| 1,677,337 | A * | 7/1928 | Grove | 606/180 |
| 4,646,738 | A | 3/1987 | Trott | |
| 5,529,580 | A * | 6/1996 | Kusunoki et al. | 606/170 |
| 5,549,637 | A * | 8/1996 | Crainich | 606/207 |
| 5,669,926 | A | 9/1997 | Aust et al. | |
| 5,752,973 | A | 5/1998 | Kieturakis | 606/207 |
| 5,851,208 | A * | 12/1998 | Trott | 606/80 |
| 5,851,212 | A | 12/1998 | Zirps et al. | |
| 6,464,711 | B1 | 10/2002 | Emans et al. | |
| 6,790,210 | B1 * | 9/2004 | Cragg et al. | 606/80 |
| 6,913,613 | B2 * | 7/2005 | Schwarz et al. | 606/206 |
| 7,585,300 | B2 * | 9/2009 | Cha | 606/80 |
| 2004/0181249 | A1* | 9/2004 | Torrance et al. | 606/170 |
| 2005/0165420 | A1 * | 7/2005 | Cha | 606/150 |
| 2005/0261692 | A1* | 11/2005 | Carrison et al. | 606/79 |

(Continued)

FOREIGN PATENT DOCUMENTS

| | | |
|---|---|---|
| DE | 4323756 A1 | 1/1995 |
| DE | 10036108 A1 | 11/2001 |

(Continued)

*Primary Examiner* — Sarah W Aleman
(74) *Attorney, Agent, or Firm* — Panitch Schwarze Belisario & Nadel LLP

(57) ABSTRACT

An endoscopic instrument includes a rigid hollow shank (2) and a tool (8) at the distal instrument end. The tool (8) is driven in rotation via a drive shaft (14), which is guided within the hollow shank (2). At the distal end of the hollow shank (2), the tool (8) projects out of the hollow shank (2), where it may be angled with respect to the distal end of the hollow shank (2).

12 Claims, 3 Drawing Sheets

(56) References Cited

U.S. PATENT DOCUMENTS

2006/0016853 A1* 1/2006 Racenet .................... 227/176.1
2008/0004643 A1* 1/2008 To et al. ........................ 606/159

FOREIGN PATENT DOCUMENTS

| | | |
|---|---|---|
| DE | 10324844 A1 | 12/2004 |
| WO | 03/022162 A1 | 3/2003 |

* cited by examiner

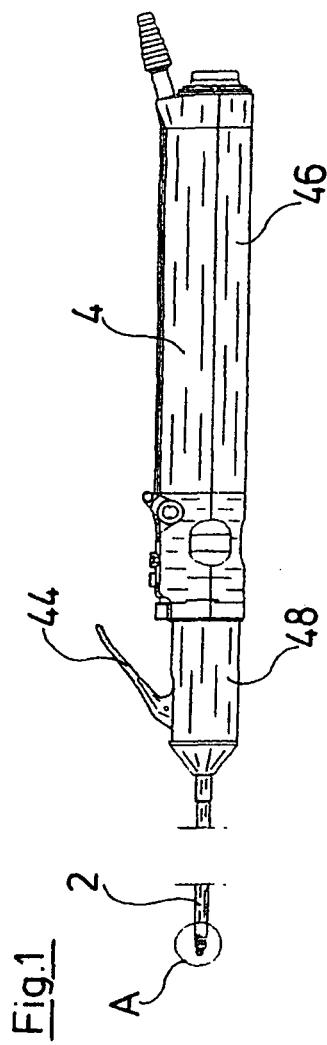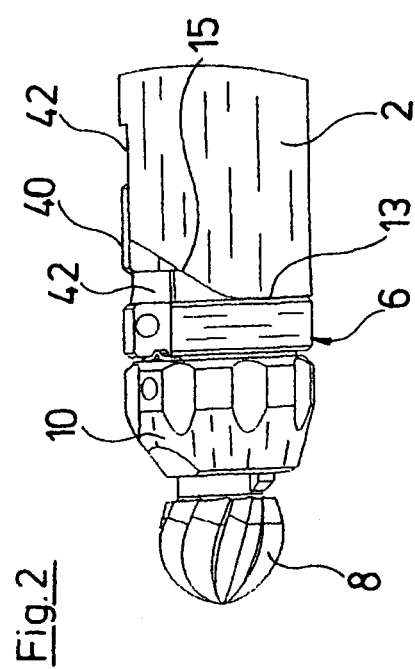

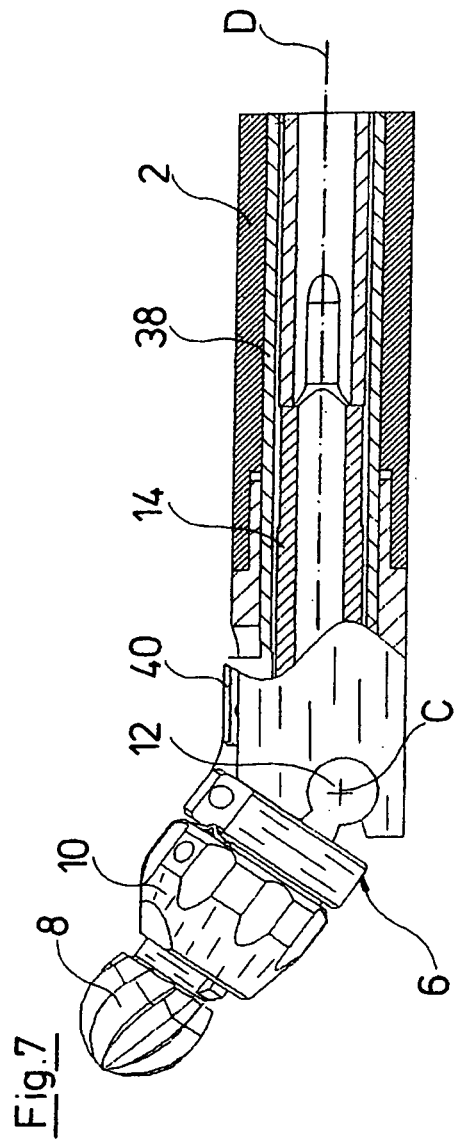
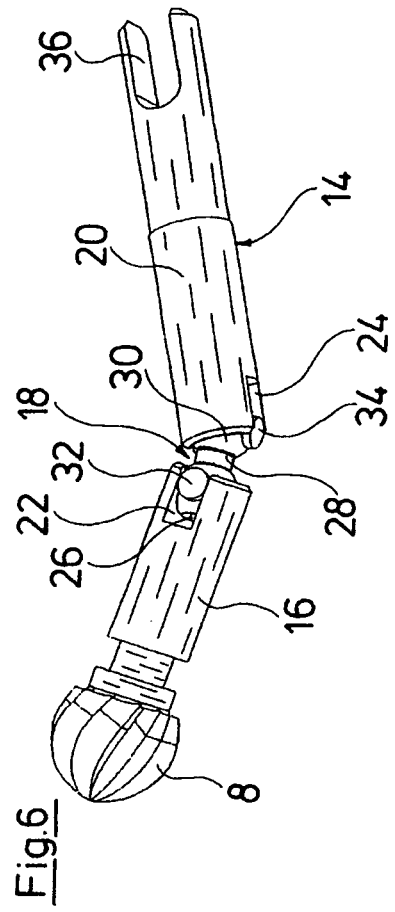
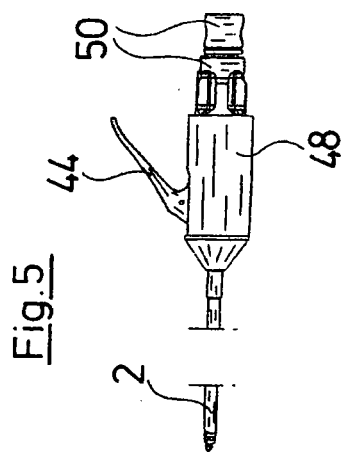

ENDOSCOPIC INSTRUMENT

BACKGROUND OF THE INVENTION

The invention relates to an endoscopic instrument for removing material, tissue and the like, and having a rigid hollow shank and a tool at the distal instrument end, the tool being driven in rotation via a drive shaft led into the hollow shank.

Instruments are known from the field of medicine, which may be introduced into body cavities via natural or artificially created access channels, in order to remove tissue there with these instruments. Such instruments usually comprise a hollow shank, which may be introduced through the access channel into the body cavity, at whose distal end a rotating tool for removing tissue is arranged in the extension of the hollow shank. Particularly with narrow access channels these instruments come up against limitations, when the tissue to be removed is located laterally of an access axis defined by the access channel.

Instruments are known in which the distal end region, with a tool located thereon, is designed in a rigidly angled manner. Such instruments are described, for example, in U.S. Pat. Nos. 1,677,337 and 4,646,738, as well as German published patent application DE 43 23 756 A1. These instruments with a rigidly angled hollow shank end and tool, however, are not suitable for endoscopic application, since they may not be led through a straight working channel of an endoscope.

Instruments which are basically suitable for this are described in U.S. Pat. Nos. 5,669,926; 5,851,212 and 6,464,711. These instruments have a straight hollow shank, which may be led through the straight working channel of an endoscope. The hollow shanks, with the tool arranged thereon, may be curved transversely away from their original longitudinal axis, for removing body tissue situated laterally of the hollow shank. However, the bending radius of the hollow shanks with these instruments is relatively large, so that the tools arranged at the distal end of the hollow shank may lie outside the scope of endoscopic optics, and an operative operation carried out with these instruments must, as a rule, be observed with additional optical means. A further disadvantage of these instruments lies in the fact that on application of a tool operated in a rotating manner, a drive shaft led through the hollow shank must likewise be bendable, i.e., must be designed in a flexible manner, whereby only relatively small torques at simultaneously low rotation speeds may be transmitted with these drive shafts. For this reason, these instruments are not suitable for removal of hard tissue, such as bone material.

BRIEF SUMMARY OF THE INVENTION

Against this background, it is an object of the invention to provide an endoscopic instrument for removing material, tissue and the like, which may be carried out by a straight working channel of an endoscope. It should also be simultaneously suitable for the removal of hard material and tissue, which may also be arranged laterally of an extension of the working channel of the endoscope.

According to the invention, this object is achieved by an endoscopic instrument, as described above, in which a tool projecting out at the distal end of the hollow shank may be angled with respect to the distal end of the hollow shank.

The endoscopic instrument according to the invention comprises a rigid hollow shank and a tool at the distal instrument end. The tool may be rotatably driven via a drive shaft guided within the hollow shank. According to the invention, the tool at the distal end of the hollow shank projects out of the hollow shank, where it may be angled with respect to the distal end of the hollow shank.

That is, the tool may be angled from a first tool position, in which it forms a straight-line extension of the hollow shank, transverse to its longitudinal axis or rotation axis, into at least one second tool position. Designed in such a manner, the endoscopic instrument according to this embodiment of the invention, on the one hand, may be guided in a first tool position through the working channel of an endoscope to its working region within the cavity, and on the other hand, with this tool it is possible in an angled tool position, to remove material or tissue in a region which is located laterally of an extension of the longitudinal axis of the hollow shank or working channel of the endoscope. With the tool only being angled, and not regions of the hollow shank, the tool is located within the field of view of the optics of the endoscope, even in the angled tool position, so that the tool may be positioned exactly to or on the material or tissue to be removed.

The tool, via suitable coupling means, is coupled in movement to the drive shaft, advantageously in a manner such that it may be driven by the drive shaft in the first as well as the second tool position. With regard to the tool, it may be, for example, a milling tool or a drilling tool or a so-called shaver.

An endoscopic instrument in the context of one embodiment of the present invention may also be a technoscope for technical machining tasks for material removal in otherwise difficulty accessible cavities of machines, motors and the like. Preferably, with regard to the instrument according to the invention, however, it is an endoscopic instrument used in a medical manner, which may be introduced via the working channel of an endoscope for the removal of tissue, in particular bone material in a human or animal body.

Preferably, the tool is arranged in a head part for mounting the tool. This head part is articulated on the distal end of the hollow shank. The head part forms a receiver for the tool at the outer side of the distal end of the hollow shank. The tool is mounted and fastened in a preferably rotatably movable manner in this receiver. The head part, in the region of the distal end of the hollow shank, is preferably pivotable about an axis aligned transversely to the longitudinal axis of the hollow shank. The head part may be moved from a position, in which the tool mounted in the head part is arranged in the extension of the longitudinal axis of the hollow shank, into a position, in which the tool is angled with respect to the longitudinal axis of the hollow shank.

Advantageously, a universal joint is provided in order to be able to actively connect the tool to the drive shaft guided in the hollow shank, also in this position, which is angled with respect to the hollow shank. The universal joint couples the tool in movement to the drive shaft in a direct or indirect manner. The universal joint permits the tool to be angled with respect to the drive shaft led into the hollow shank. Thus, the drive shaft and the tool may be arranged in an axially equal manner in a first position, while the rotation axis of the tool in a second position may be angled with respect to the rotation axis of the drive shaft. The universal joint, on account of its great stiffness in the rotation direction, permits the transmission of relatively large torques in both positions, even at large rotation speeds, which permits the removal of hard material or tissue, in particular the removal of bone tissue.

The tool may be coupled directly to the universal joint. Preferably, however, the drive shaft is divided into at least two parts, wherein the universal joint is arranged between two drive shaft parts. With this design the universal joint connects a proximal-end drive shaft part, actively connected to a drive motor, to a distal-end drive shaft part which is coupled in movement to the tool.

Usefully, a grip part is provided at the proximal end of the instrument according to one embodiment of the invention. The drive shaft may be coupled in movement to the drive motor in this grip part. In order to be able to ensure a cleaning of the endoscopic instrument according to hygienic demands, the drive shaft may also be designed such that it may be divided on the distal end of the grip part and on the proximal end of the universal joint part. Here, a shaft part on the grip part side and at least one shaft part on the hollow shank side may be provided, wherein these two drive shaft parts are preferably designed such that they may be connected to one another with a positive fit.

In order to be able to move the tool into a position which is angled with respect to the distal end of the hollow shank, the head part is usefully coupled in movement via a joint part to an actuation rod, which is movable in the hollow shank in the axial direction. The joint part is preferably articulated on the distal end of the actuation rod and on the head part, wherein on the head part it is usefully also displaceable in a direction transversely to the longitudinal axis of the head part. With this design, having only one device consisting of the actuation rod and the joint part, it is advantageously possible by displacing the actuation rod in the axial direction of the hollow shank, to pivot the head part with the tool arranged therein, into a position which is angled to the distal end of the hollow shank, as well as back into a position which is flush with the hollow shank.

The instrument according to one embodiment of the invention advantageously comprises on the proximal side a handle which is coupled in movement to the actuation rod, for displacing the actuation rod in the hollow shank. This handle is preferably provided on a grip part, which is arranged on the proximal side of the instrument and is coupled in movement to the actuation rod. With regard to the handle, it may be, for example, an actuation lever or actuation slider, by which the head part, with the tool mounted therein, may be moved into a position which is angled with respect to the end of the hollow shank, as well as into a position which is flush with the distal end of the hollow shank. Preferably, the handle is designed as a lever.

In particular, if the endoscopic instrument according to the invention is envisaged for the medical field, a channel may advantageously be designed within the hollow shank, by which tissue particles separated in an operation area may be sucked away, or by which rinsing fluid may be supplied to the operation area. This channel usefully runs out in the region of the distal end of the hollow shank. Its proximal end is usefully conductingly connected to suction means or means for supplying a rinsing fluid. In a preferred design, the drive shaft arranged within the hollow shank forms the channel for supplying and/or leading away rinsing fluid. That is, with this design, the drive shaft is designed as a hollow shank.

In a further preferred design, the actuation rod forms a channel for supplying and/or leading away rinsing fluid. Accordingly, the actuation rod in this case is preferably designed as a tube.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings:

FIG. 1 is a schematic, lateral view of an endoscopic instrument according to one embodiment of the invention;

FIG. 2 is an enlarged representation of the detail A from FIG. 1;

FIG. 5 is a schematic, lateral view of a distal end region of the instrument according to FIG. 1, which may be decoupled;

FIG. 6 is a schematic, lateral view of a drive shaft with a tool of the instrument according to FIG. 1, which is arranged thereon; and FIG. 7 is a partly sectioned, lateral view of the distal end region of the instrument according to FIG. 1.

DETAILED DESCRIPTION OF THE INVENTION

Figure 3:
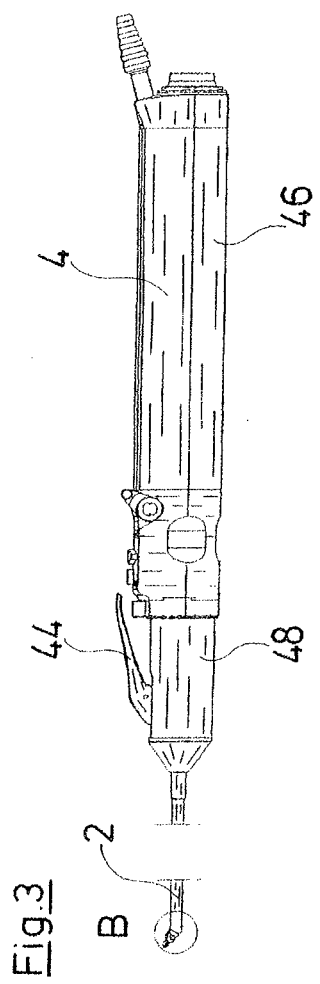
FIG. 3 is a schematic, lateral view of the endoscopic instrument according to FIG. 1, shown with a tool in an angled position.

The endoscopic instrument represented in the figures comprises a rigid hollow shank 2. This hollow shank 2 is arranged on the distal end of a grip part 4. The hollow shank 2 forms the part of the endoscopic instrument via which the working channel of an endoscope, which is not shown, is introduced into the inside of a body. A head part 6 is arranged outside the distal end of the hollow shank 2, and a tool in the form of a miller head 8 is mounted in this head part. The head part 6 at its distal end comprises a closure element 10 with which the miller head 8 may be releasably fastened in the head part 6. For this, a clamping device is provided in the closure element 10, with which device the miller head 8 may be firmly clamped with a non-positive fit.

Figure 4:
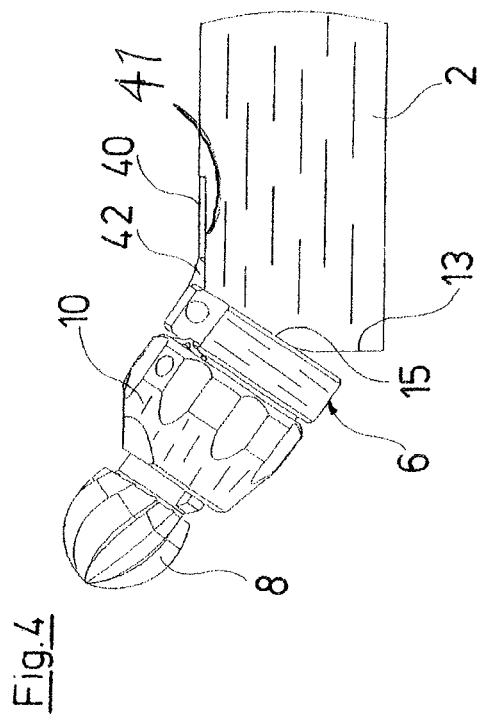
FIG. 4 is an enlarged representation of the detail B of FIG. 3.

The head part 6 is pivotably mounted about an axis C on a joint 12 at the distal end of the hollow shank 2 (see FIG. 7). The axis C extends normally to a longitudinal axis D of the hollow shank 2. The pivotability of the head part 6 permits the miller head 8 to be angled with respect to the distal end of the hollow shank 2. In order to be able to angle the head part 6 with respect to the distal end of the hollow shank 2, the distal end-side of the hollow shank 2 is partially beveled. Thus, a region 13 of the distal end of the hollow shank 2 is aligned normally to the longitudinal axis D of the hollow shank 2, while a region 15 connecting thereto runs obliquely to this. If the head part 6 and the miller head 8 mounted therein are arranged in a direct extension of the hollow shank 2, then the proximal end of the head part 6 bears on the region 13. It comes to bear on the region 15 in the angled position of the head part 6 (see FIG. 4).

The miller head 8 is actively connected to a drive motor arranged in the grip part 4, by way of a hollow drive shaft 14 (see FIG. 6). The drive shaft 14 is designed of several parts, wherein a distal drive shaft part 16, into which the miller head 8 engages with a positive fit, is connected via a universal joint 18 to a drive shaft part 20, which connects thereto on the proximal end and which is connected in drive to the drive motor arranged in the grip part 4.

The drive shaft part 16 at its proximal end comprises a slot 22 running perpendicularly to the end-face there, and the drive shaft part 20 at its distal end comprises a slot 24 running perpendicular to the end-face there, for forming the universal joint 18.

Apart from this, a dumbbell-shaped joint part is provided, with which a spherical body 26 is connected via a web 28 to a spherical body 30. A pin 32 is led through the spherical body 26 in a manner such that the two ends of the pin 32 respectively project out of the spherical body 26. The pin 32 is aligned transversely to the web 28, which connects the spherical bodies 26 and 30 to one another. In a similar manner, a pin 34 is led through the spherical body 30 and the distal ends of the pin also respectively project from the spherical body 30. The pin 34 is also aligned transversely to the web 28, wherein however it is offset by essentially 90.degree. with respect to the pin 32. The spherical body 26 engages into the proximal end of the hollow drive shaft part 16 for connecting the drive shaft parts 16 and 20, wherein the ends of the pin 32 are guided in the slot 22 of the drive shaft part 16. In a similar manner, the spherical body 30 engages into the distal end of the likewise hollow drive shaft part 20, wherein the ends of the pin 34 are guided in the slot 24 designed on the drive shaft part 20.

The drive shaft part 20 at its proximal end comprises a slot 36 running transversely over the entire end-face. This slot serves for coupling to a further grip-side drive shaft part, which is not represented and which at its distal end comprises a projection corresponding with the slot 36 and engaging into the slot 36 with a positive fit, in the form of a claw clutch, for coupling this drive shaft part to the drive shaft part 20.

An actuation rod 38 (see FIG. 7) is provided for bending the head part 6 with the miller head 8 mounted therein, at an angle. This actuation rod 38 is arranged within the hollow shank 2 between the drive shaft 14 and the inner wall of the hollow shank 2. At the distal end, the actuation rod 38 comprises an end piece 40, which widens to the outside in the radial direction of the hollow shank with respect to the actuation rod 38, and which is guided in a longitudinal slot 41 provided at the distal end of the hollow shank 2. A joint part 42 is articulated on the end-piece 40 of the actuation rod 38. The joint part 42 is also articulated on the head part 6 on the end-piece 40 of the actuation rod, distanced to the articulation.

The actuation rod 38 is displaceably guided in the hollow shank 2 in the direction of the longitudinal axis D. The actuation rod 38 is actuated by way of a handle in the form of a lever 44, which is arranged on the grip part 4. The head part 6, by a movement of the actuation rod 38 in the proximal direction, is brought into its angled position, in which it bears on the region 15 of the distal end of the hollow shank 2. If the actuation rod 38 is moved in the distal direction, the head part 6 pivots back again into such a position, in which it is arranged in the direct extension of the hollow shank 2.

The grip part 4 of the endoscopic instrument is designed in a dividable manner and comprises a proximal-side grip part 46 and a distal-side grip part 48 (see FIG. 3). The drive motor of the instrument is arranged in the grip part 46 of this instrument. At the distal side, the hollow shank 2, with the head part 6 and the miller head 8, connects to the grip part 48. Moreover, the lever 44 for actuating the actuation rod 38 is arranged on the grip part 48. Coupling means 50 (see FIG. 5) are provided on the grip part 48 for the releasable connection of the grip parts 46 and 48, as well as for the releasable coupling of the drive shaft 14 to the drive motor.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. An endoscopic instrument for removal of material, the instrument comprising:
   a rigid hollow shank defining a longitudinal axis and a tool at a distal instrument end,
   a head part directly connecting a proximal end of the tool to a distal end of the hollow shank,
   wherein the tool projects axially beyond a distal end of the head part along the longitudinal axis and the tool includes a first position in which the tool forms a straight line extension of the longitudinal axis and a second position in which the tool is angled with respect to the longitudinal axis,
   the tool being driven in rotation by a drive shaft guided in the hollow shank, the drive shaft including a distal drive shaft part and a proximal drive shaft part,
   a dumbbell-shaped first joint part including a first spherical body, a second spherical body spaced-apart therefrom along the longitudinal axis, and a web connecting the first and second spherical bodies, the first spherical body received in a hollow proximal end of the distal drive shaft part, the second spherical body received in a hollow distal end of the proximal drive shaft part,
   a single actuation rod being movable in the hollow shank in an axial direction of the hollow shank and having a second joint part movably coupling the head part to the single actuation rod, the second joint part being articulated on the single actuation rod and on the head part, such that by axial movement of the single actuation rod in a proximal direction the tool is brought into the second position, and by axial movement of the single actuation rod in a distal direction the tool is brought into the first position.

2. The endoscopic instrument according to claim 1, wherein the instrument on a proximal end comprises a handle, which is coupled in movement to the single actuation rod.

3. The endoscopic instrument according to claim 2, wherein the single actuation rod forms a channel for supplying and/or leading away rinsing fluid.

4. The endoscopic instrument according to claim 1, wherein the tool is coupled in movement in a direct or indirect manner to the drive shaft via a universal joint, and wherein the universal joint is the first joint part.

5. The endoscopic instrument according to claim 1, wherein at least one channel is formed within the hollow shank, the at least one channel running out in a region of the distal end of the hollow shank.

6. The endoscopic instrument according to claim 1, wherein the drive shaft forms a channel for supplying and/or leading away rinsing fluid.

7. The endoscopic instrument according to claim 1, wherein the head part further includes a closure element for releasably fastening the tool in the head part.

8. The endoscopic instrument according to claim 1, further comprising:
   a first pin extending through the first spherical body such that opposing ends of the first pin project outwardly from the first spherical body, and
   a second pin extending through the second spherical body such that opposing ends of the second pin project outwardly from the second spherical body,
   wherein each of the first and second pins is aligned transversely to the web.

9. The endoscopic instrument according to claim 8, wherein the distal drive shaft part includes a first slot at the proximal end thereof, and wherein the proximal drive shaft part includes a second slot at the distal end thereof, the opposing ends of the first pin being guided in the first slot and the opposing ends of the second pin being guided in the second slot.

10. An endoscopic instrument comprising:
   a rigid hollow shank defining a longitudinal axis and a tool at a distal instrument end, a longitudinal slot extending radially through the hollow shank at a distal end of the hollow shank and being open to outside of the hollow shank,
   a head part directly connecting a proximal end of the tool to a distal end of the hollow shank, wherein the tool projects axially beyond a distal end of the head part along the longitudinal axis and the tool includes a first position in which the tool forms a straight line extension of the longitudinal axis and a second position in which the tool is angled with respect to the longitudinal axis
   a drive shaft guided in the hollow shank, the drive shaft rotatably driving the tool, the drive shaft including a distal drive shaft part and a proximal drive shaft part, a proximal end of
   the distal drive shaft part including a first slot therein, and a distal end of the proximal drive shaft part including a second slot therein,
   a dumbbell-shaped first joint part including a first spherical body, a first pin extending through the first spherical body such that opposing ends of the first pin project outwardly from the first spherical body, the opposing ends of the first pin being guided in the first slot of the distal drive shaft part, a second spherical body spaced apart from the first spherical body along the longitudinal axis, and a second in extending through the second spherical body such that opposing ends of the second in project outwardly from the second spherical body, the opposing ends of the second in being guided in the second slot of the proximal drive shaft part,
   an actuation rod being movable in the hollow shank in an axial direction of the hollow shank, a distal end of the actuation rod comprising an end piece guided in the longitudinal slot at the distal end of the hollow shank, and
   a second joint part being articulated on the end piece of the actuation rod, the second joint part also being articulated on the head part, such that by axial movement of the actuation rod in a proximal direction the tool is brought into the second position, and by axial movement of the actuation rod in a distal direction the tool is brought into the first position.

11. The endoscopic instrument according to claim 10, further comprising:
   a web connecting the first spherical body to the second spherical body, wherein each of the first and second pins is aligned transversely to the web.

12. The endoscopic instrument according to claim 10, wherein the end piece widens radially to the outside of the hollow shank through the longitudinal slot.

* * * * *